(12) United States Patent
Bain et al.

(10) Patent No.: US 7,879,048 B2
(45) Date of Patent: *Feb. 1, 2011

(54) SUTURE CAPTURE DEVICE

(75) Inventors: Gregory H. Bain, Laguna Niguel, CA (US); Norman S. Gordon, Irvine, CA (US)

(73) Assignee: ArthroCare Corporation, Austin, TX (US)

( * ) Notice: Subject to any disclaimer, the term of this patent is extended or adjusted under 35 U.S.C. 154(b) by 101 days.

This patent is subject to a terminal disclaimer.

(21) Appl. No.: 10/856,716

(22) Filed: May 28, 2004

(65) Prior Publication Data
US 2004/0236353 A1 Nov. 25, 2004

Related U.S. Application Data

(63) Continuation of application No. 10/308,732, filed on Dec. 3, 2002, now Pat. No. 6,770,084.

(60) Provisional application No. 60/391,676, filed on Jun. 26, 2002.

(51) Int. Cl.
A61B 17/04 (2006.01)
A61B 17/12 (2006.01)

(52) U.S. Cl. ....................................... 606/144

(58) Field of Classification Search ............... 606/139, 606/144, 148
See application file for complete search history.

(56) References Cited

U.S. PATENT DOCUMENTS

| 919,138 | A |   | 4/1909 | Drake et al. |
|---|---|---|---|---|
| 1,635,066 | A | * | 7/1927 | Wells ........................ 606/145 |
| 2,289,983 | A |   | 1/1942 | Wappler ..................... 604/61 |
| 2,286,578 | A |   | 6/1942 | Sauter ....................... 606/148 |
| 2,738,790 | A | * | 3/1956 | Todt, Sr. et al. ............ 606/145 |

(Continued)

FOREIGN PATENT DOCUMENTS

CA 2205176 12/2000

(Continued)

OTHER PUBLICATIONS

U.S. Appl. No. 10/352,655, filed Jan. 28, 2003, Tran et al.

(Continued)

*Primary Examiner*—(Jackie) Tan-Uyen T Ho
*Assistant Examiner*—Dianne Dornbusch
(74) *Attorney, Agent, or Firm*—Matthew Scheele; Brian Szymczak

(57) ABSTRACT

A suturing instrument for placing mattress stitches in soft tissue, such as a rotator cuff, includes an elongate shaft with both a stationary jaw and a movable jaw disposed at the distal end thereof. The shaft is coupled to a handle grip at the proximal end, which is configured to manipulate the jaws into open and closed positions. The jaws are configured to allow for a traumatic grasping of soft tissues. The stationary jaw may include a molded tip that holds and positions opposite ends of a single strand of suture material. The serrated upper jaw is configured to grasp and immobilize the tissue to be sutured. Hooked needles are movably positioned to pierce the grasped and immobilized tissues, and to engage and retrieve the opposite ends of the single strand of suture material. The handle is released to open the moveable jaw, whereupon the instrument may be withdrawn, trailing the suture, and leaving a mattress stitch in the grasped tissue.

19 Claims, 7 Drawing Sheets

U.S. PATENT DOCUMENTS

| | | | |
|---|---|---|---|
| 3,842,840 A * | 10/1974 | Schweizer | 606/145 |
| 3,946,740 A | 3/1976 | Bassett | |
| 4,109,658 A | 8/1978 | Hughes | 128/340 |
| 4,164,225 A * | 8/1979 | Johnson et al. | 606/145 |
| 4,345,601 A | 8/1982 | Fukuda | 128/339 |
| 4,373,530 A | 2/1983 | Kilejian | 128/334 R |
| 4,493,323 A | 1/1985 | Albright et al. | 128/340 |
| 4,621,640 A | 11/1986 | Mulhollan et al. | |
| 4,635,637 A | 1/1987 | Schreiber | 128/337 |
| 4,738,255 A | 4/1988 | Goble et al. | 128/92 YF |
| 4,741,330 A | 5/1988 | Hayhurst | 128/43 R |
| 4,781,182 A | 11/1988 | Purnell et al. | 128/92 |
| 4,836,205 A | 6/1989 | Barrett | |
| 4,923,461 A | 5/1990 | Caspari | |
| 4,926,860 A | 5/1990 | Stice et al. | 606/146 |
| 4,935,027 A | 6/1990 | Yoon | |
| 4,957,498 A | 9/1990 | Caspari | |
| 4,981,149 A | 1/1991 | Yoon et al. | 128/898 |
| 5,037,422 A | 8/1991 | Hayhurst et al. | 606/72 |
| 5,037,433 A | 8/1991 | Wilk et al. | 606/139 |
| 5,046,513 A | 9/1991 | Gattuma et al. | 128/898 |
| 5,059,201 A * | 10/1991 | Asnis | 606/144 |
| 5,085,661 A | 2/1992 | Moss | 606/139 |
| 5,217,471 A | 6/1993 | Burkhart | 606/148 |
| 5,222,977 A | 6/1993 | Esser | 606/223 |
| 5,269,786 A | 12/1993 | Morgan | 606/96 |
| 5,304,184 A | 4/1994 | Hathaway et al. | 606/144 |
| 5,312,422 A | 5/1994 | Trott | |
| 5,318,577 A | 6/1994 | Li | 606/147 |
| 5,336,229 A | 8/1994 | Noda | 606/144 |
| 5,397,325 A | 3/1995 | Della Badia et al. | 112/169 |
| 5,403,329 A | 4/1995 | Hinchcliffe | 606/147 |
| 5,409,494 A | 4/1995 | Morgan | 606/96 |
| 5,417,699 A | 5/1995 | Klein et al. | 606/148 |
| 5,431,666 A | 7/1995 | Sauer et al. | 606/139 |
| 5,445,167 A | 8/1995 | Yoon et al. | 128/898 |
| 5,454,823 A | 10/1995 | Richardson et al. | 606/148 |
| 5,474,565 A | 12/1995 | Trott | |
| 5,480,405 A | 1/1996 | Yoon | 606/139 |
| 5,499,991 A | 3/1996 | Garman et al. | |
| 5,522,820 A * | 6/1996 | Caspari et al. | 606/148 |
| 5,527,322 A | 6/1996 | Klein et al. | 606/144 |
| 5,573,542 A | 11/1996 | Stevens | 606/144 |
| 5,575,801 A | 11/1996 | Habermeyer et al. | 606/144 |
| 5,609,597 A | 3/1997 | Lehrer | 606/139 |
| 5,613,974 A | 3/1997 | Andreas et al. | 606/144 |
| 5,618,290 A | 4/1997 | Toy et al. | 606/139 |
| 5,626,590 A | 5/1997 | Wilk | 606/148 |
| 5,645,552 A | 7/1997 | Sherts | 606/145 |
| 5,665,108 A | 9/1997 | Galindo | 606/215 |
| 5,690,653 A * | 11/1997 | Richardson et al. | 606/148 |
| 5,700,273 A * | 12/1997 | Buelna et al. | 606/144 |
| 5,741,281 A | 4/1998 | Martin | 606/148 |
| 5,776,150 A | 7/1998 | Nolan et al. | 606/148 |
| 5,779,719 A | 7/1998 | Klein et al. | 606/144 |
| 5,792,151 A * | 8/1998 | Heck et al. | 606/144 |
| 5,792,152 A | 8/1998 | Klein et al. | 606/144 |
| 5,792,153 A | 8/1998 | Swain et al. | 806/144 |
| 5,797,927 A | 8/1998 | Yoon | 606/144 |
| 5,836,956 A * | 11/1998 | Buelna et al. | 606/148 |
| 5,860,991 A | 1/1999 | Klein et al. | 606/144 |
| 5,860,992 A | 1/1999 | Daniel et al. | 606/145 |
| 5,902,311 A | 5/1999 | Andreas et al. | 606/144 |
| 5,904,692 A | 5/1999 | Steckel et al. | 606/139 |
| 5,908,426 A * | 6/1999 | Pierce | 606/139 |
| 5,921,994 A | 7/1999 | Andreas et al. | 606/144 |
| 5,947,982 A * | 9/1999 | Duran | 606/139 |
| 5,980,538 A * | 11/1999 | Fuchs et al. | 606/145 |
| 5,984,933 A | 11/1999 | Yoon | 606/148 |
| 6,001,109 A | 12/1999 | Kontos | 606/148 |
| 6,022,360 A | 2/2000 | Reimels et al. | 606/144 |
| 6,024,747 A * | 2/2000 | Kontos | 606/144 |
| 6,036,699 A | 3/2000 | Andreas et al. | 606/139 |
| 6,048,351 A | 4/2000 | Gordon et al. | 605/144 |
| 6,051,006 A | 4/2000 | Shluzas et al. | 606/148 |
| 6,059,801 A | 5/2000 | Samimi | 606/148 |
| 6,096,051 A | 8/2000 | Kortenbach et al. | 606/144 |
| 6,117,144 A * | 9/2000 | Nobles et al. | 606/144 |
| 6,136,010 A * | 10/2000 | Modesitt et al. | 606/144 |
| 6,143,004 A * | 11/2000 | Davis et al. | 606/144 |
| 6,217,592 B1 * | 4/2001 | Freda et al. | 606/145 |
| 6,245,079 B1 * | 6/2001 | Nobles et al. | 606/144 |
| 6,332,889 B1 * | 12/2001 | Sancoff et al. | 606/148 |
| 6,533,795 B1 | 3/2003 | Tran et al. | 606/144 |
| 6,551,330 B1 * | 4/2003 | Bain et al. | 606/144 |
| 6,605,096 B1 | 8/2003 | Ritchart | 606/144 |
| 6,770,084 B1 | 8/2004 | Bain et al. | 606/144 |
| 6,893,448 B2 * | 5/2005 | O'Quinn et al. | 606/139 |
| 6,896,686 B2 * | 5/2005 | Weber | 606/145 |
| 6,911,034 B2 * | 6/2005 | Nobles et al. | 606/144 |
| 6,984,237 B2 * | 1/2006 | Hatch et al. | 606/144 |
| 7,090,686 B2 | 8/2006 | Nobles et al. | 606/144 |
| 7,160,309 B2 * | 1/2007 | Voss | 606/144 |
| 7,198,631 B2 * | 4/2007 | Kanner et al. | 606/139 |
| 7,377,926 B2 * | 5/2008 | Topper et al. | 606/144 |
| 7,449,024 B2 * | 11/2008 | Stafford | 606/144 |
| 7,585,305 B2 * | 9/2009 | Dreyfuss | 606/144 |
| 7,758,597 B1 | 7/2010 | Tran et al. | 606/144 |
| 2002/0147456 A1 | 10/2002 | Diduch et al. | 606/144 |
| 2003/0065337 A1 | 4/2003 | Topper et al. | 606/144 |
| 2003/0083695 A1 * | 5/2003 | Morris et al. | 606/222 |
| 2003/0181925 A1 | 9/2003 | Bain et al. | 606/144 |
| 2003/0195528 A1 | 10/2003 | Ritchart | 606/144 |
| 2003/0220658 A1 * | 11/2003 | Hatch et al. | 606/139 |
| 2003/0233106 A1 | 12/2003 | Dreyfuss | 606/144 |
| 2004/0010273 A1 | 1/2004 | Diduch et al. | 606/144 |
| 2004/0236353 A1 | 11/2004 | Bain et al. | 606/139 |
| 2004/0249394 A1 * | 12/2004 | Morris et al. | 606/144 |
| 2005/0165419 A1 | 7/2005 | Sauer et al. | 606/148 |
| 2008/0097482 A1 | 4/2008 | Bain et al. | 606/144 |
| 2010/0241144 A1 | 9/2010 | Delli-Santi | 606/150 |

FOREIGN PATENT DOCUMENTS

| | | |
|---|---|---|
| DE | 4235602 A1 | 4/1994 |
| DE | 2532242 A1 | 7/1995 |
| EP | 0535908 A2 | 4/1993 |
| WO | 91/06247 | 5/1991 |
| WO | 97/10756 | 3/1997 |

OTHER PUBLICATIONS

PCT International Search Report for PCT/US01/42186, Mailed Feb. 13, 2002.
PCT International Preliminary Examination Report for PCT/US01/42186 3pgs, Sep. 9, 2003.
PCT International Search Report for PCT/US02/22889 2 pgs, Mailed May 8, 2003.
PCT International Preliminary Examination Report for PCT/US02/22889 3 pgs, Jan. 15, 2003.
PCT International Search Report for PCT/US03/18540 1 pg, Mailed Oct. 15, 2003.
PCT International Preliminary Examination Report for PCT/US03/18540, Aug. 24, 2004.
European Search Report for EP 02752446 5pgs., Oct. 12, 2009.
European Examination Report for EP 037419405 4pgs, Jan. 11, 2010.

* cited by examiner

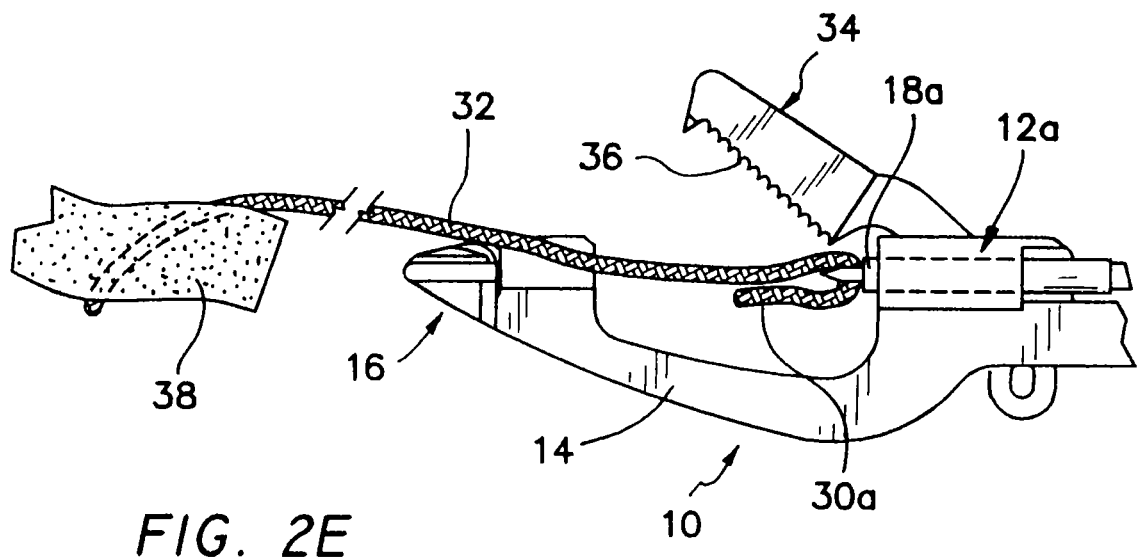
FIG. 2E
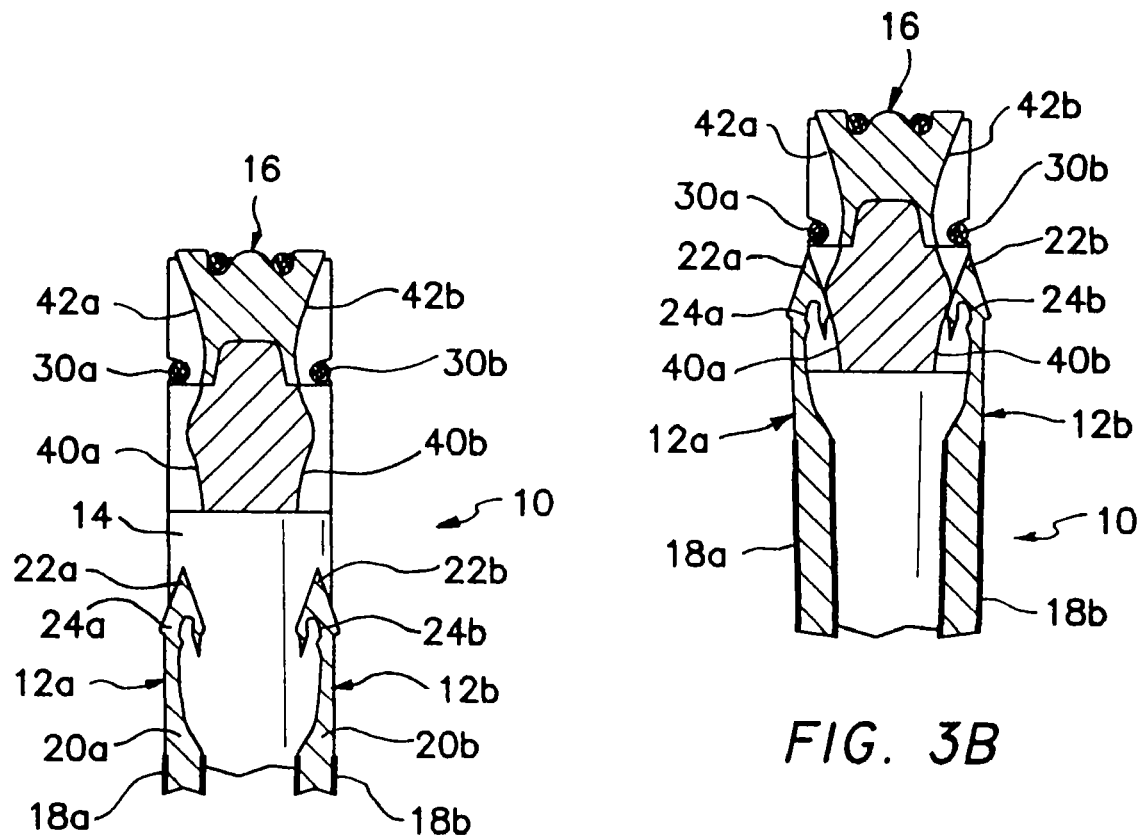
FIG. 3A
FIG. 3B

SUTURE CAPTURE DEVICE

This application is a continuation under 35 U.S.C. 120 of U.S. patent application Ser. No. 10/308,732, filed on Dec. 3, 2002, now U.S. Pat. No. 6,770,084, which claims the benefit under 35 U.S.C. 119(e) of Provisional U.S. Application Ser. No. 60/391,676, entitled *Suture Capture Device*, and filed on Jun. 26, 2002, wherein both of these applications are expressly incorporated herein by reference.

BACKGROUND OF THE INVENTION

The present invention relates to a method and apparatus for placing sutures in soft tissue, and more particularly to methods and devices for arthroscopic repair of a torn rotator cuff.

Suturing of body tissues is a time consuming aspect of most surgical procedures. Many surgical procedures are currently being performed where it is necessary to make a large opening to expose the area of, for instance, the human body that requires surgical repair. There are instruments that are becoming increasingly available that allow the viewing of certain areas of the body through a small puncture wound without exposing the entire body cavity. These viewing instruments, called "endoscopes", can be used in conjunction with specialized surgical instrumentation to detect, diagnose, and repair areas of the body that were previously only able to be repaired using traditional "open" surgery. In the past, there have been many attempts to simplify the task of driving a needle carrying suture through body tissues to approximate, ligate and fixate them. Many prior disclosures, such as described in U.S. Pat. No. 919,138 to Drake et al, employ a hollow needle driven through the tissue with the suture material passing through the hollow center lumen. The needle is withdrawn, leaving the suture material in place, and the suture is tied, completing the approximation. A limitation of these types of devices is that they are particularly adapted for use in open surgical procedures where there is ample room for the surgeon to manipulate the instrument.

Others have attempted to devise suturing instruments that resemble traditional forceps, such as U.S. Pat. No. 3,946,740 to Bassett. These devices pinch tissue between opposing jaws and pass a needle from one jaw through the tissue to the other jaw. Graspers then pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

The term "endosurgery" means "endoscopic surgery", or surgery performed using an endoscope. In conjunction with a video monitor, the endoscope permits the surgeon to remotely visualize the operative site. Operations using an endoscope are significantly less invasive when compared to traditional open surgery. Patients usually return home the next day, or in some cases, the same day of the endosurgical procedure. This is in contrast to standard open surgical procedures where a large incision divides the muscle layers and allows the surgeon to directly visualize the operative site. Patients may stay in the hospital for 5 to 6 days or longer following open surgery. In addition, after endosurgical procedures, patients return to work within a few days versus the traditional 3 to 4 weeks recuperative period at home following open surgery.

Access to the operative site using endosurgical or minimally invasive techniques is accomplished by inserting small tubes, known as trocars, into a body cavity. These trocars have a diameter of, for example, between 3 mm and 30 mm and a length of about 150 mm (6 inches). There have been attempts to devise instruments and methods for suturing within a body cavity through these trocar tubes.

Such an instrument is disclosed by U.S. Pat. No. 4,621,640 to Mulhollan et al. Mulhollan et al. describe an instrument that may be used to hold and drive a needle, but make no provision for retrieval of the needle from the body cavity, nor the completion of the suture by tying. The instrument disclosed by Mulhollan et al. is limited, in that the arc through which the needle must be driven is perpendicular to the axis of the device.

Another such instrument, intended for endoscopic use, is described in U.S. Pat. No. 4,935,027 to Yoon. This instrument uses oppositional hollow needles or tracks pushed through the tissue and adapted to create a tract through which the suture material is pushed. It is not clear how these curved tracks would be adapted to both be able to pierce the tissue planes illustrated, parallel to the tips of the tracks, and be curved toward each other to form the hollow tract.

Yet another instrument and method is shown by Caspari in U.S. Pat. No. 4,923,461 issued May 8, 1990 and U.S. Pat. No. 4,957,498 issued Sep. 18, 1990. The Caspari patents disclose an endoscopic instrument suitable for use through a trocar that resembles the Yoon approach, but with a single hollow needle on one of a set of oppositional jaws. The jaws simultaneously close, grasping the tissue. The jaw opposite the hollow needle has a window through which the hollow needle passes as the jaws close, freeing the lumen of the hollow needle from the tissue. Much like Yoon, a suture or suture snare is pushed down through the lumen and retrieved from the suture site, the jaws released, and the suture pulled back out through the trocar. This device may be used to place simple stitches in tissues that have been mobilized and have an edge accessible to the jaws. A limitation of the device is the manipulation that must be done with the snare if a suture other than a monofilament is used.

Another instrument specifically adapted for the orthopedic surgeon for the repair of a torn anterior cruciate ligament or for meniscal repair is disclosed in U.S. Pat. No. 4,836,205 to Barrett. Barrett combines in a single instrument the functions of grasping the tissue to be sutured and the passing of the needles through that tissue. It is to be understood that this instrument is designed for use specifically under endoscopic view, and through trocars as previously described. A fairly generic endoscopic grasper is disclosed that has been adapted to allow for a hollow lumen from the handle of the grasper down to the distal tip of the grasper jaws. An elongate needle of 8 to 10 inches in length may be passed through this hollow lumen. The needle, being significantly longer than the grasper, is introduced through the handle of the grasper, and may be driven through the tissue being held in the grasping jaws of the device. The needle is then retrieved from the tissue via a trocar port placed substantially opposite the port through which the grasper is introduced. If a mattress stitch is desired, two needles attached to opposite ends of a suture are both passed through the tissue and retrieved. A limitation of this device is that there must be both visual and physical access to both sides of the tissue flap to be sutured. This requires trocars to be placed opposite each other and roughly on a line intercepting the tissue. This is a severe limitation in the instance of shoulder repair, and specifically in repair of the rotator cuff.

Yet another instrument adapted for use in endoscopic procedures is described by Garman et al in U.S. Pat. No. 5,499, 991. This instrument has an elongated housing provided with a needle tip and a lateral opening near the sharpened needle tip. A suture engaging hook, typically formed from wire, is extendable through the lateral opening and away from the axis of the elongated housing by virtue of being predisposed to bend away from the axis in order to snare the suture. The hook is situated at the distal end of an elongated flexible support which is pre-formed in order to enable the hook to be laterally displaced from the axis of the needle tip when the support is moved distally relative to the lateral opening. When a suture is engaged by the hook, the hook is retracted proximally in order to place and hold the suture adjacent the lateral opening. The instrument is somewhat limited in the case of rotator cuff repair in that an additional instrument would need to be introduced into the joint to immobilize the tissues sufficiently to allow the needle tip to penetrate the tissues to be sutured. Also, no provision is made for capturing the two ends of a suture to place a mattress stitch, save repeating the prior steps.

A similar instrument is disclosed in U.S. Pat. Nos. 5,312,422 and 5,474,565 issued to Trott. These patents also describe a needle structure adapted for penetration of soft tissues and suture retrieval. A substantially flat suturing needle with a hook feature is illustrated which can engage a suture to an outer housing, thereby presenting a relatively smooth surface at the distal end of the needle to minimize tissue trauma. The limitations mentioned above are evident here as well. The requirement for additional instrumentation to immobilize the tissues, and the lack of provision for a mattress stitch are paramount. There have been other attempts to improve the methods of tissue repair. These include the development of staplers and anchoring devices. In response to some of the aforementioned problems in placing sutures in tissues endoscopically, manufacturers have developed tissue staplers. These devices utilize stainless steel or titanium staples that are constructed much like the staples used to hold papers together. The major disadvantage of these kinds of staplers is that they leave metal in the body. For some tissues this is not a problem, however in some procedures, metal staples left within the tissues can be a major hindrance to the healing process.

Orthopedic surgeons have begun to explore alternatives to the traditional open approach for the many indications requiring reconstruction of some aspect of the shoulder. As they did in adopting minimally invasive approaches to knee repair and reconstruction, the use of either an endoscope or a "mini-open" approach is gaining in popularity with surgeons, patients and third party payers. It is an increasingly common problem for tendons and other soft, connective tissues to tear or to detach from associated bone. One such type of tear or detachment is a "rotator cuff" tear, causing pain and loss of ability to elevate and externally rotate the arm. Complete separation can occur if the shoulder is subjected to gross trauma, but typically, the tear begins as a small lesion, especially in older patients.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally using instruments and techniques such as the Caspari punch previously described. This creates a simple stitch instead of the more desirable mattress or Mason-Allen stitch. Rather than thread the suture through trans-osseous tunnels which are difficult or impossible to create arthroscopically using current techniques, an anchor is driven into bone at a location appropriate for repair. The repair is completed by tying the cuff down against bone using the anchor and suture.

Early results of less invasive techniques are encouraging, with a substantial reduction in both patient recovery time and discomfort. However, as mentioned, this approach places only one loop of suture in the cuff for each anchor, reducing the fundamnental strength of the repair. The knots in the tendon can be bulky and create a painful impingement of the tendon on the bone. This is because the knots end up on top of the cuff, in the sub-acromial space, and have the opportunity to rub on the acromion as the arm is raised. Because non-absorbable suture materials are used for these types of repairs, the suture and associated knots are not absorbed into the body, and hence provide a constant, painful reminder of their presence. None of the prior art devices are adaptable to effect the placement of a mattress stitch in grasped tissues, nor are they adaptable to place sutures precisely and controllably while making provision for needle retrieval when using endoscopic techniques. None of the prior art devices make it possible to place a mattress stitch into, for example, the supraspinatus tendon utilizing an endoscopic approach.

What is needed, therefore, is a family of novel suturing devices that overcome the above described disadvantages of prior known devices in a simple and economical manner. The devices should be capable of arthroscopically creating a mattress stitch in a tendon to increase the soft tissue pullout strength of the repaired tendon.

SUMMARY OF THE INVENTION

Accordingly, the inventors have developed a new and novel approach to securing a mattress stitch in a tissue flap. An instrument that combines the function of both grasping the tissue and passing sutures through the tissue to form a mattress stitch is herein described. The instrument includes a pair of grasping jaws that oppose each other along a line substantially perpendicular to the long axis of the instrument. The distal end of the instrument incorporates the fixed jaw, and proximal to that jaw is a moveable jaw that is controlled by the user via a lever on the handgrip.

In a preferred method of the present invention the instrument is inserted through a portal known as a trocar cannula. The portal is created by first making an incision in the skin, and then inserting a cannula through the incision to the repair site. The distal end of the instrument is inserted through the cannula under direct visualization from a second trocar cannula that has been previously inserted. The visualization is accomplished via an endoscope, of a type well known in the art. The instrument is inserted until the jaws reach, for example, torn rotator cuff tissue. In operation, the distal end of the grasper aspect of the instrument is positioned at the repair site underneath the tissue to be grasped. The moveable jaw pivots toward the stationary jaw by squeezing the handle lever. The handle lever moves inward by pivoting about a pivot pin. Once the appropriate section of tissue is isolated and grasped by the jaws, the lever may be locked in its closed position using a latch mechanism.

Once the surgeon is satisfied with the placement of the grasper on the grasped tissue, the surgeon can then deploy the suture needles to create a mattress stitch in the tissues, for example, the above-mentioned torn rotator cuff. In operation, the suture needles may be advanced through the grasped tissues by pulling on a second lever. The lever is directly connected to the needles via a connecting rod, and the lever is pulled against the force of a return spring. In turn, the connecting rod pushes a needle carriage, with suture needles held in the carriage. The needle carriage resides behind the proximal moveable jaw of the instrument, and, at the urging of the lever via the connecting rod, is able to move distally with the needles passing around the moveable jaw. As the carriage moves distally, the tips of the suture needles begin to clear the distal edge of apertures created in a more proximal portion of the stationary jaw, and begin to penetrate through the top of the grasped tissue and advance distally towards the more distal portion of the stationary jaw.

The stationary distal jaw incorporates two apertures that are adapted to receive the ends of the suture. Secondary open channels perpendicular to the suture apertures are configured with a specific geometry designed to direct the suture needles across the apertures containing the ends of the sutures. As the suture needles approach the end of their stroke, the distal ends of the needles have passed completely through the grasped tissues and begin to enter the secondary open channels in the stationary distal jaw.

At this point, any pull force being applied by the grasper on the grasped tissues is relaxed. Once the tissue is in a relaxed state, the jaws of the grasper are then opened. The handle lever is unlocked from the locking mechanism and returns to an open position due to the pull force exerted on it by means of a return spring. As the return spring pulls on the lever, it pivots about a pin.

To complete the pull out of the suture needles, it is necessary to pull on the grasper, and to remove it from the repair site. The instrument can be retracted back through the portal via the trocar cannula. As the instrument is removed from the suture site, the free ends of the suture are retrieved as well. This causes the suture to pass through the tissues at the puncture sites. As the suture is pulled through, the loop end of the suture is pulled snug against the underside of the tissues to form what is referred to as a mattress stitch. This process may be repeated as necessary, depending on the number sutures required for the particular procedure being undertaken.

Now it may be seen by those skilled in the art, that the combination of grasping tissues to be sutured and precisely placing a mattress stitch in the grasped tissues, while working through a trocar port, effects a significant advance in the art. Advantages of the present invention thus include providing an endoscopic instrument adapted for the grasping of tissues and creating a mattress stitch within those tissues, as well as the provision of a suturing instrument that allows for the reloading of additional sutures for placement of subsequent stitches. Additionally, the inventive system is advantageous in that it provides for direct capture of the suture material.

More particularly, there is provided in one preferred embodiment of the present invention a suturing device, comprising a distal portion which is engaged with a length of suture, as well as a needle which is axially movable distally and proximally. A soft tissue receiving portion, preferably comprising a clamp having first and second jaws, wherein one of the first and second jaws is movable relative to the other to grasp soft tissue therein, is disposed proximally of the distal portion. A ramp portion for moving the needle radially inwardly and outwardly as the needle moves axially over the ramp portion is also provided.

In a preferred embodiment, the distal portion for retaining the suture comprises a suture cartridge with a molded tip, having grooves for accommodating the suture. The ramp portion comprises a radially outwardly sloping entrance ramp for moving the needle radially outwardly as the needle moves axially in a distal direction, as well as a radially inwardly sloping retraction ramp for moving the needle radially inwardly as the needle moves axially in a proximal direction. The needle comprises a distal point, a proximal shaft, and a hook defining a suture holding area.

The hook portion of the needle is uniquely designed to provide a positive tactile indication as to when the suture has been capture within the suture holding area. This design includes a terminus of the hook, which is cantilevered proximally from a distal end of the needle. A bump on the needle in a location opposed to the hook terminus is provided, so that the hook terminus and the bump together provide a tactile sensation to a user when suture passes thereover into the suture holding area.

In preferred embodiments, a second needle, as well as a second ramp portion, is provided, so that a mattress stitch may be created. A sheath, which is slidable relative to the needle, is provided for selectively covering each needle, particularly when the needle is being retracted proximally through the soft tissue, to prevent unnecessary damage thereto.

In another aspect of the invention, there is provided a needle for a suturing device, which comprises a distal point, a proximal shaft, and a hook defining a suture holding area. As noted above, the needle preferably further comprises a terminus of the hook, which is cantilevered proximally from a distal end of the needle, as well as a bump on the needle in a location opposed to the hook terminus.

In still another aspect of the invention, there is described a method of suturing soft tissue using a suturing device, which comprises steps of retaining a portion of soft tissue to be sutured, and moving a needle having a hook which defines a suture holding area distally, so that the hook is disposed in a location past the portion of soft tissue and past a length of suture which is retained on a distal portion of the suturing device. Then, the needle is moved proximally in order to capture the suture so that it is retained in the suture holding area. Once the suture is captured, the needle is moved a further distance proximally, so that the needle draws the suture through the portion of soft tissue, thereby suturing the soft tissue. Preferably, when the needle is moved distally, it is also moved radially outwardly in order to avoid contacting, and possibly damaging, the length of suture. Additionally, when the needle is moved proximally, it is also moved radially inwardly in order to ensure proper capture of the suture. In preferred methods, it is further desirable to cover the needle with a sheath prior to retracting the needle proximally through the soft tissue.

The invention, together with additional features and advantages thereof, may best be understood by reference to the following description taken in conjunction with the accompanying illustrative drawing.

BRIEF DESCRIPTION OF THE DRAWINGS

FIGS. 2A through 2E are detail side views of the distal end of the instrument of FIGS. 1A through 1E, which again illustrate the general structure and operation of the present invention;

FIGS. 3A through 3E are cross sectional plan views of the distal end of the instrument of FIGS. 1A through 1E, showing the relationship between the body structure and the needle geometry;

DESCRIPTION OF THE PREFERRED EMBODIMENT

Figure 1A:
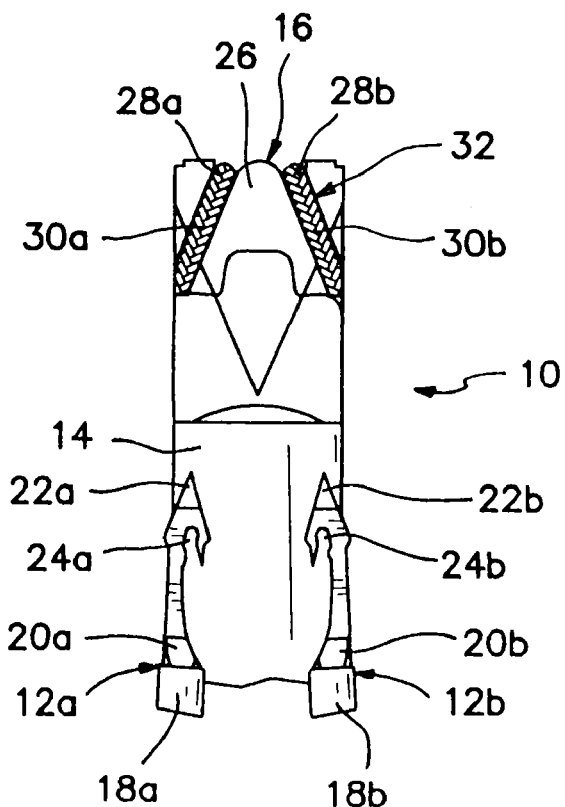
FIGS. 1A through 1E are detail plan views of the distal end of an instrument constructed in accordance with the principles of the present invention, illustrating the general structure and operation of the instrument.

The present invention relates to a method and apparatus for the arthroscopic repair of torn tissue and bone at a surgical repair site using an inventive device which is a combination tissue grasper and suture placement device. Although the present invention is described primarily in conjunction with the repair of a torn rotator cuff, the apparatus and method could also be used in arthroscopic repair at other sites, such as the knee, elbow, hip surgery, and for other surgical techniques for securing suture in the soft tissues of the body.

A description of the basic functional elements of suture capture and retrieval, in accordance with the principles of the invention, follows.

Referring to FIGS. 1A through 1E, there may be seen a plan view of the distal end of a suturing device 10 that includes a pair of needles 12a and 12b, a lower jaw 14, and a suture cartridge 16. The needles 12a, 12b further include sliding tubes or sheaths 18a and 18b, needle shafts 20a and 20b, needle points 22a and 22b, and hooks 24a and 24b. The suture cartridge 16 comprises a molded tip 26 with grooves 28a and 28b, into which the two ends 30a and 30b of a length of suture are threaded.

Figure 1B:
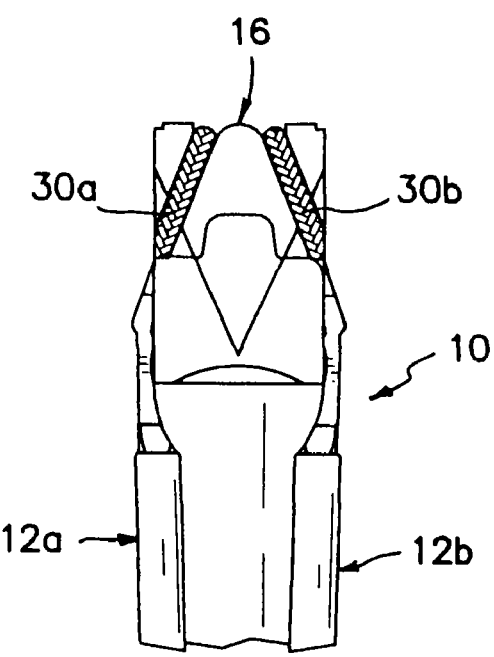

Referring to FIG. 1B, the needles 12a, 12b are advanced distally toward the suture cartridge 16 in preparation for capture and retrieval of the two ends 30a, 30b of the length of suture. It is to be understood that the entire length of the suture which includes the two ends 30a, 30b is not seen in this illustration. The loop of suture between the two ends 30a, 30b trails beneath the distal end of the suturing device 10 and is thus not visible. It will be described more fully later how the capture of the two ends of a suture can be used to create what is known in the art as a mattress stitch.

Figure 1C:
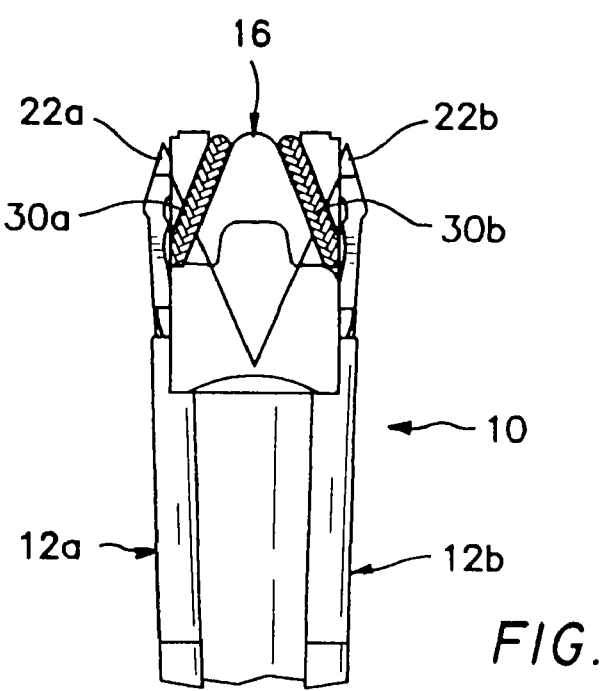
Figure 1D:
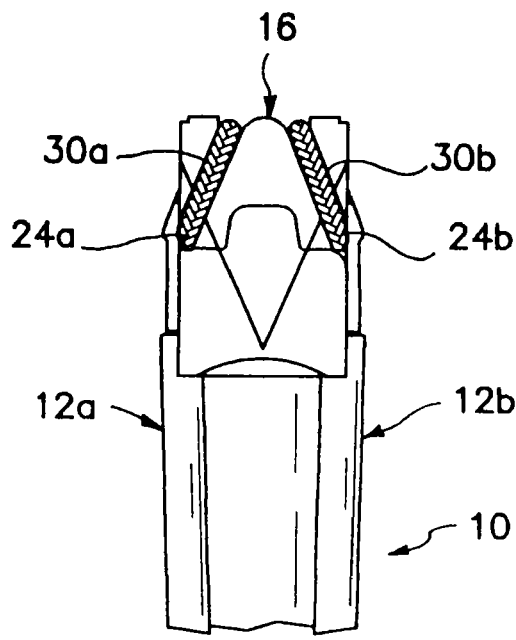
Figure 1E:
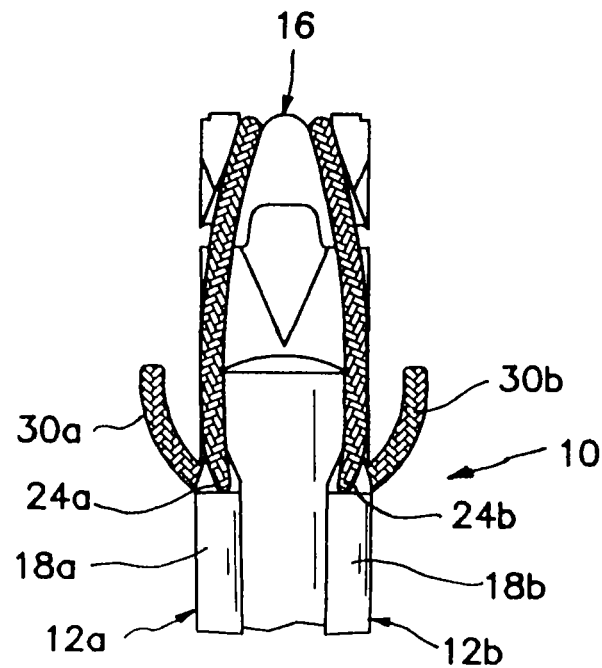

Referring now to FIG. 1C, it may be seen that the needles 12a, 12b are further advanced distally toward the suture cartridge 16 and past the two ends 30a, 30b of the suture, placing the hooks 24a, 24b in position past the two suture ends 30a, 30b in preparation for capture. As it may be seen in FIG. 1D, as the needles 12a, 12b are retracted proximally, the hooks 24a, 24b engage the two suture ends 30a, 30b and capture them for retrieval. As the needles 12a, 12b are further retracted proximally as shown in FIG. 1E, the sliding tubes 18a, 18b, held stationary by frictional forces exerted by tissue (not shown), cover the hooks 24a, 24b and assist in the engagement of the two ends 30a, 30b.

Having understood the basic structure and nature of the suture retrieval mechanism, a more complete disclosure of how this mechanism may be used to place a stitch, and more specifically, a mattress stitch, in soft tissues will now be described. Referring now to FIGS. 2A through 2E, there may be seen detail side views of the same suturing device 10 as described in FIGS. 1A through 1E. The inventive device 10 includes the suture ends 30a, 30b of a single strand of suture 32, and an upper jaw 34, which includes teeth 36. Referring now to FIG. 2B, soft tissue 38 is introduced into the space between the upper jaw 34 and the lower jaw 14. By means of a mechanism not discussed or shown herein, but of a type well known to those skilled in the art, the upper jaw 34 is pivoted about an axis, causing it to clamp or grasp the soft tissue 38 and immobilize it between the teeth 36 of the upper jaw 34 and the lower jaw 14. Referring now to FIG. 2C, it may be seen that the needles 12 have been advanced distally through the soft tissue 38 and in engagement with the suture cartridge 16 with the needle points 22a, 22b advancing beyond the suture ends 30a, 30b.

It is to be understood that in this view, only one needle 12a of the two needles 12a 12b may be visualized, but that a concomitant needle 12b is penetrating the tissue along a substantially parallel path, as previously illustrated in FIG. 1C. The relative position of the needles 12a, 12b in FIGS. 1C and 2C is substantially the same. As seen in FIG. 2D, the needles 12a, 12b are retracted proximally, trailing the suture 32 by virtue of having captured the suture ends 30. In this way, the suture 32 is placed through the soft tissue. Referring to FIG. 2E, it may be seen that the upper jaw 34 has been pivoted away from the soft tissue 38, allowing the suturing device 10 to be retracted away from the soft tissue 38, pulling the suture 32 completely through the soft tissue 38. The result of this action is the placement of a mattress stitch in the grasped tissues in a manner similar to that previously described.

As will now be shown, there are certain characteristics, geometries and interfaces between parts that combine to optimize the performance of the suture capture mechanism. Repeatable capture of the suture material, as well as minimizing damage to the suture ends are objects of the present invention. By referring to FIGS. 3A through 3E, the specific methods and devices that facilitate suture capture in accordance with the principles of the invention will be described.

Figure 2A:
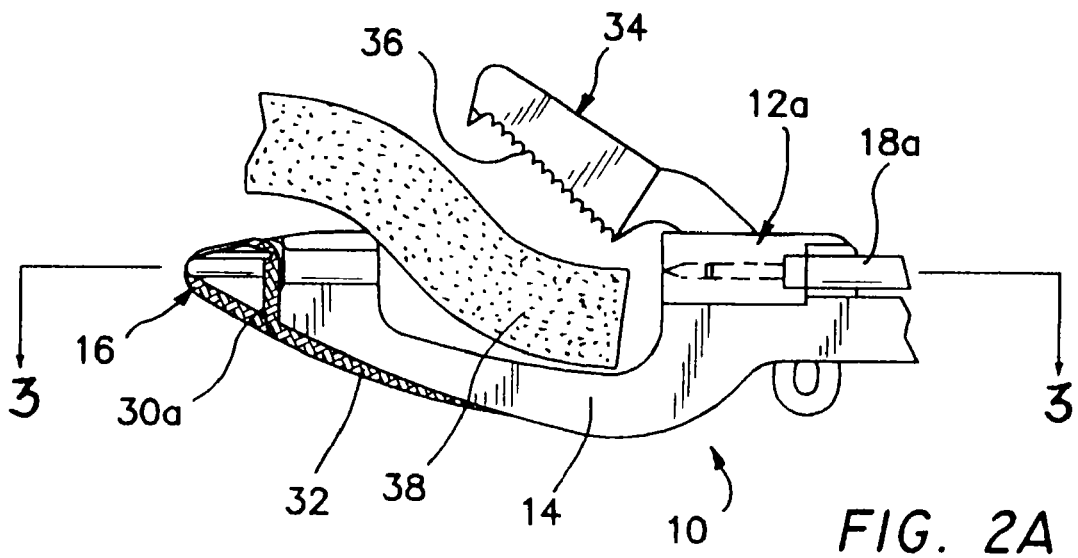
Figure 2B:
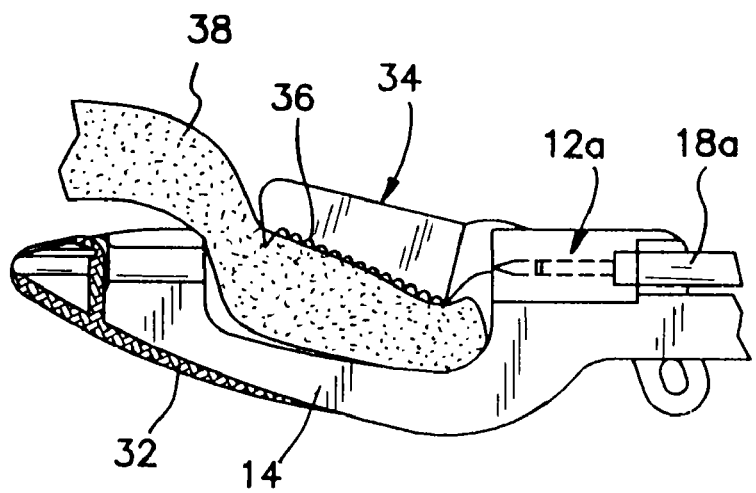
Figure 2C:
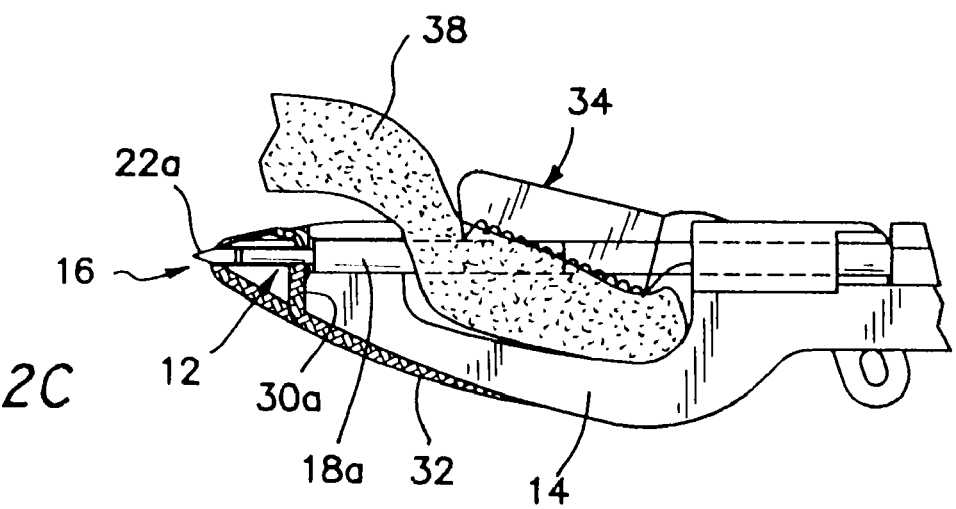
Figure 2D:
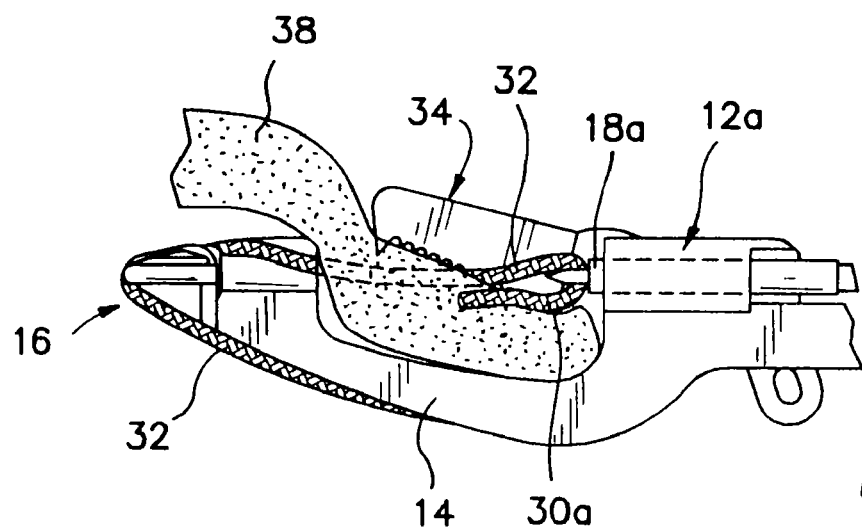
Figure 3C:
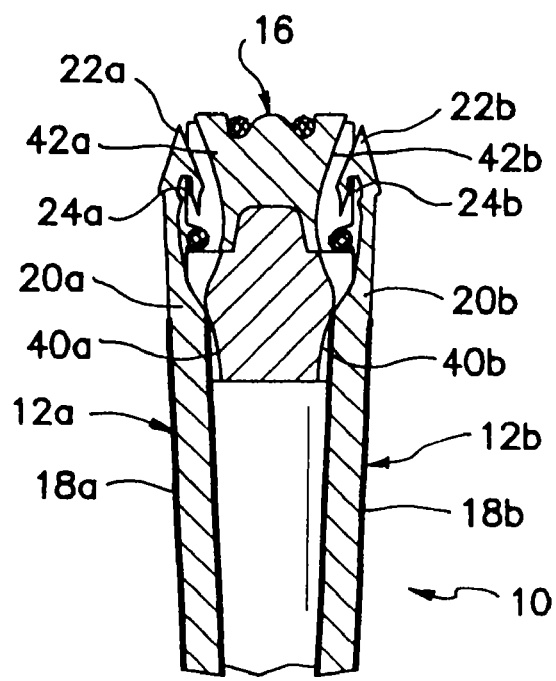

FIGS. 3A through 3E depict cross sections taken along the lines 3-3 in FIG. 2A. Referring now to FIG. 3A, there is seen the suture device 10 which includes the needles 12a, 12b, lower jaw 14, suture cartridge 16, and suture ends 30a, 30b. The upper jaw 34 and the soft tissue 38 have not been shown in these figures for clarity. It is possible to now see entrance ramps 40a, 40b and retraction ramps 42a, 42b that are in the path of the needles 12a, 12b. By referring to FIG. 3B, it may be seen that as the needles 12a, 12b move distally in the direction of the suture cartridge 16, the tips of the needles 12a, 12b engage the entrance ramps 40a, 40b. The engagement with the entrance ramps 40a, 40b deflects the needles 12a, 12b such that the needle points 22a, 22b are directed over and away from the suture ends 30a, 30b, preventing the needle points 22a, 22b from piercing or otherwise damaging the suture ends 30a, 30b. Further distal movement of the needles 12a, 12b, as shown in FIG. 3C, allows the hooks 24a, 24b to be disposed distally of the suture ends 30a, 30b and in position to capture the suture upon retraction. It is to be noted that, at this juncture, the sliding tubes 18a, 18b have entered the area of the entrance ramps 40a, 40b, and have begun to ride up the entrance ramps 40a, 40b, thus further deflecting the needles 12a, 12b.

Figure 3D:
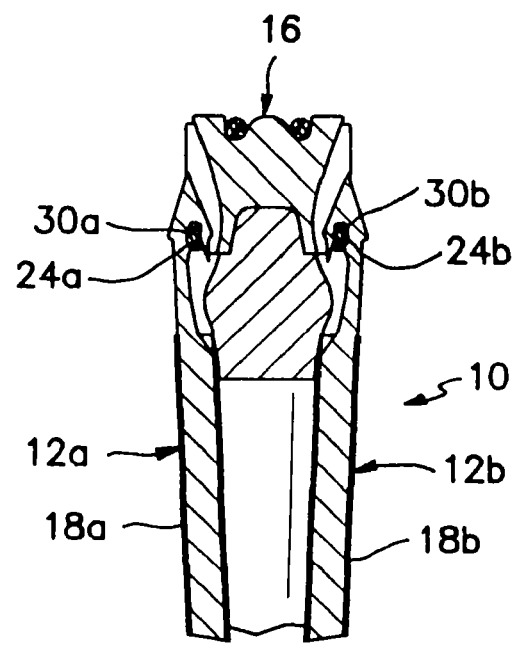
Figure 3E:
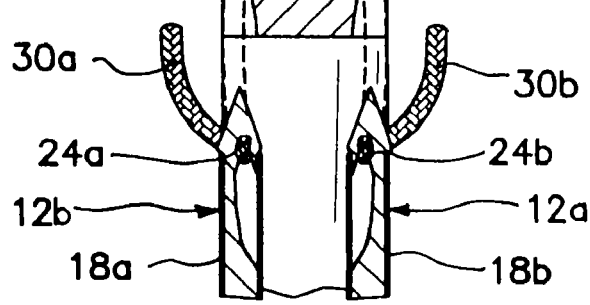

Referring now to FIG. 3D, it may be appreciated that as the needles 12a, 12b are retracted proximally, the needle hooks 24a, 24b ride down the retraction ramps 42a, 42b and under the suture ends 30a, 30b, thereby capturing the suture ends 30a, 30b in the hooks 24a,b, and allowing the suture ends 30a, 30b to be peeled away from the suture cartridge 16 and retracted proximally. It may also be appreciated that as the needle shafts 20a, 20b retract, the sliding tubes 18a, 18b remain motionless in the soft tissue (not shown), allowing the sliding tubes to cover the gap made by the hooks 24a, 24b and allowing smooth passage through the tissue. This retraction may be appreciated by comparing the position of the sliding tubes 18a, 18b relative to the hooks 24a, 24b in FIGS. 3D and 3E. Once the sliding tubes 18a, 18b have covered the gap, they retract along with the needle shafts 20a, 20b back through the soft tissue 38.

Figure 4:
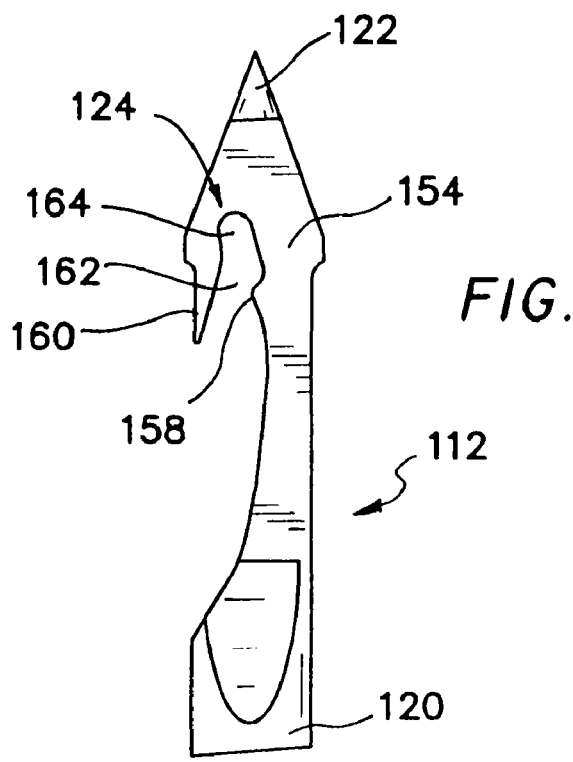
FIG. 4 is a detailed view of a needle of the present invention.
Figure 5:
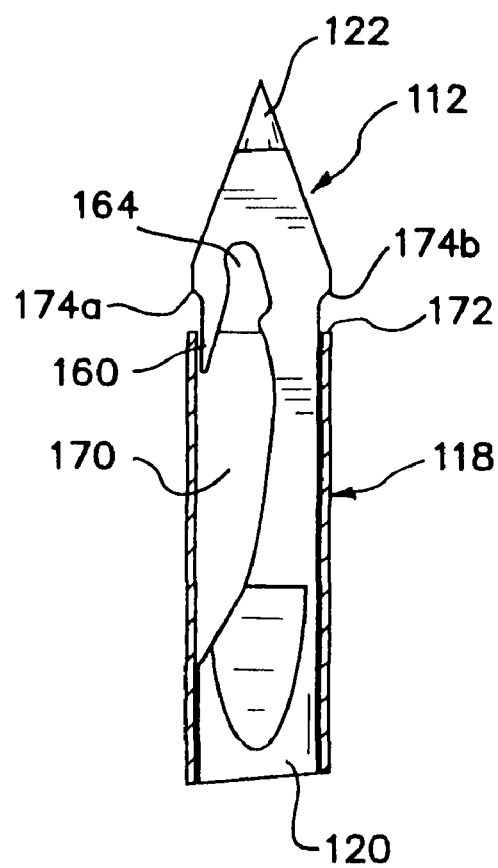
FIG. 5 is a detailed view of the needle of FIG. 4 with an associated sleeve.
Figure 9:
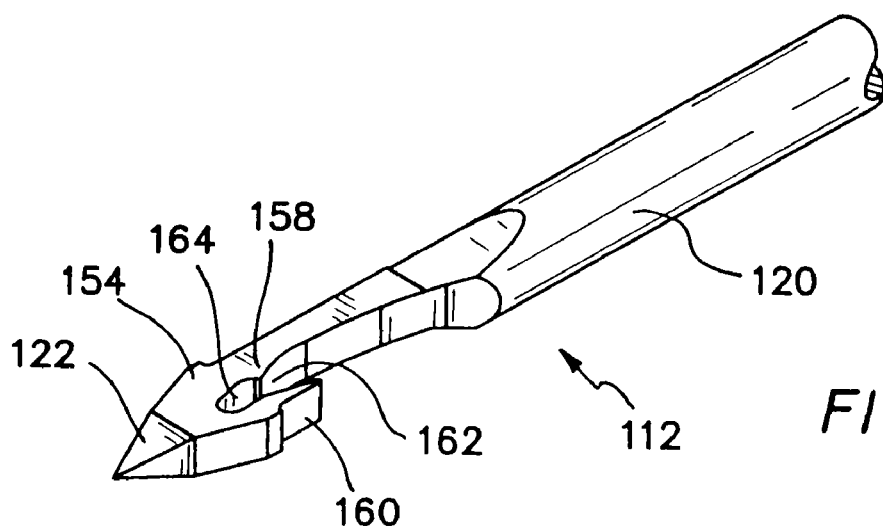
FIG. 9 is a perspective view of the needle of FIG. 4.

A more complete and detailed description of the construction and operation of the needles may be understood by referring to FIGS. 4, 5 and 9, where there may be seen, in isolation, a needle 112 constructed in accordance with the principles of the present invention, wherein like elements to those described in prior embodiments bear like reference numerals, preceded by the numeral 1. It is intended that the needles described in connection with these figures may be utilized in the embodiments shown in FIGS. 1-3. The needle 112 thus includes a needle shaft 120, and a flattened distal portion 154. The flattened distal portion 154 of the needle 112 includes a hook 124, comprising a bump 158, a hook terminus 160, a hook entrance 162, a suture holding area 164, and a needle point 122. The specific geometry of the needle 112 that is described herein is to be understood as being representative of a family of configurations that embody the design parameters that are now to be described. For instance, the needle point 122 shown herein is a beveled cutting point, but may be, for example, a conical or trocar point. Further, the position of the bump 158 may be on the opposite side of the hook entrance 162. These, and other nuances will be discussed in more detail further below.

When the needle 112 has been introduced through soft tissue (not shown) and has been driven past the suture to be captured as previously illustrated in FIGS. 1C, 2C, and 3C and has begun to be retracted back through the soft tissue, the hook terminus 160 rides along one of the retraction ramps 42a, 42b and underneath one of the ends 30a, 30b of the suture, thus forcing the suture through the hook entrance 162 and past the bump 158 into the suture holding area 164. The hook terminus 160, being cantilevered, has some flexibility, and opens slightly as the suture passes the bump 158, creating a subtle tactile sensation as the suture seats in the suture holding area 164. The suture holding area 164 is sized so that its cross sectional area is slightly smaller than the cross sectional area of the suture it is designed to capture, thus creating some compression of the captured suture by virtue of the spring loading provided by the above described deformation of the hook terminus 160.

It is important to understand that this particular configuration of needle 112, and indeed all of the needles described in connection with the present invention, are configured to capture a section of suture substantially near one of the ends of the suture. As such, and because the needle is not capturing the suture near the center of the stand of suture where the drag on both legs of the suture as it is retracted through the tissue would be equalized, it is important to prevent the suture from migrating in or through the suture holding area 164. It is also important to secure the suture in the needle while the instrument is being withdrawn, to form and complete, for example, a mattress stitch. Therefore, the combination of deformation, tactile sensation, and compression conspires to hold the suture securely.

Another aspect of the present invention that is to be understood is the mechanism described to effect smooth passage of the needle hook with captured suture back through the soft tissue as the needles are retracted. To that end, FIG. 5 illustrates the needle 112 together with a sliding tube 118, which includes an inner lumen 170, and a lumen opening 172. The sliding tube 118 is dimensioned so that the needle shaft 120 may slide freely through the inner lumen 170, but does not allow sufficient clearance between the inner lumen 170 and the needle shaft 120 to permit tissue to enter the lumen opening 172. As the needle 112 is retracted through the tissue as previously described, the sliding tube 118 remains motionless, closing the opening formed by the hook terminus 160 and the suture holding area 164. The lumen opening 170 ultimately bottoms out against needle shoulders 174a, 174b, and assists in pinching and holding any suture that may be captured in the needle hook 124.

Figure 6:
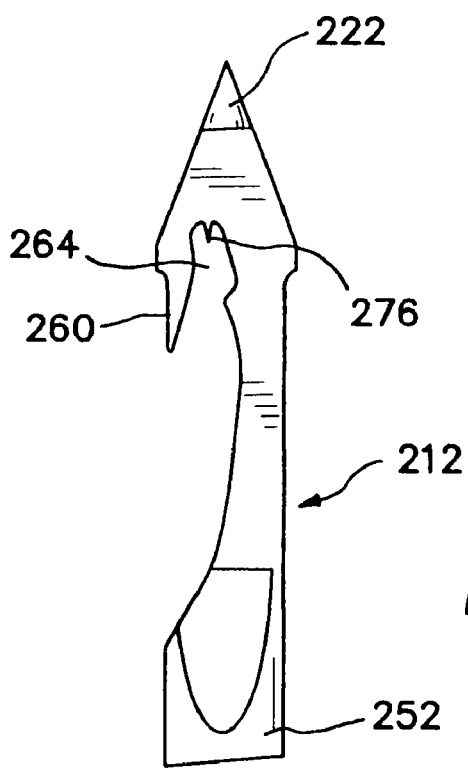
FIG. 6 is a detailed view of an alternative embodiment of a needle of the present invention.

An alternative needle embodiment is illustrated in FIG. 6, wherein like elements to those of the embodiment of FIGS. 4 and 5 are denoted by like reference numerals, except that they are increased by 100. In this embodiment, there may be found a needle 212 that has features similar to that of the needle 112 described above. In this embodiment, a barb 276 is included as part of the suture holding area 264, and is configured to penetrate the suture weave and assist in immobilizing the suture. Needle shaft is denoted in FIG. 6 by reference numeral 252

Figure 7:
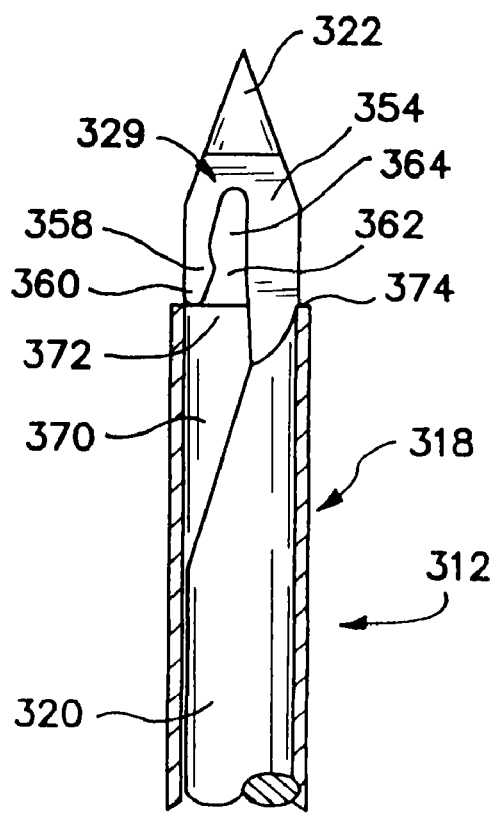
FIG. 7 is a detailed view of another alternative embodiment of a needle of the present invention.
Figure 8:
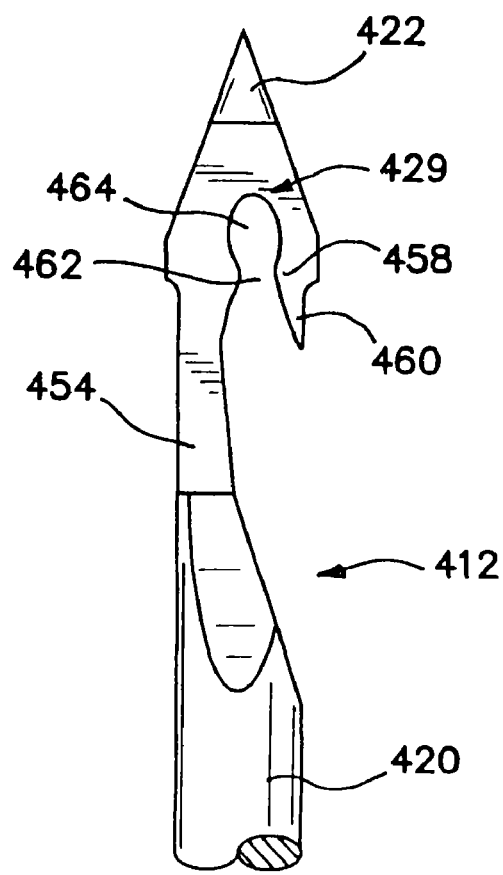
FIG. 8 is a detailed view of still another alternative embodiment of a needle of the present invention.

FIGS. 7 and 8 illustrate additional embodiments of the needle, and as above, like elements are denoted by like reference numerals, except in the case of FIG. 7, the labels are increased by 100 respective to FIG. 6, and in FIG. 8, increased by 200 respective to FIG. 6.

Accordingly, in FIG. 7 there may be seen a needle 312 that includes a needle shaft 320, and a flattened distal portion 354. The flattened distal portion 354 of the needle 312 includes a hook 329, comprising a bump 358, a hook terminus 360, a hook entrance 362, a suture holding area 364, and a needle point 322. The needle 312 is illustrated along with a sliding tube 318 which includes an inner lumen 370, and a lumen opening 372, and lumen end 374. It is important to note from this illustration that the sliding tube 318 may bottom out on the end of the hook 324 as opposed to covering it as previously described. Also, the bump 358 is shown here on the opposite side of the hook entrance 362.

Referring now to FIG. 8, there may be seen a needle 412 that includes a needle shaft 420, and a flattened distal portion 454. The flattened distal portion 454 of the needle 412 includes a hook 429, comprising a bump 458, a hook terminus 460, a hook entrance 462, a suture holding area 464, and a needle point 422. This embodiment is provided to illustrate that the suture holding area 464 may take on a shape different from that previously disclosed.

To those skilled in the art, the use of a beveled point needle may seem to solve some of the aforementioned problems of spearing the suture by creating a needle that, by virtue of its completely beveled nature, is able to smoothly move over the suture material without snagging. However, it must be noted that a beveled needle, when forced through soft tissue, has a pronounced tendency to wander, and targeting of the needle in order to place it in an advantageous position for the retrieval of the suture material is quite challenging. In fact, this wandering tendency in the direction of the bevel is uncontrollable to the degree that repeatable suture capture is not possible. Another way of ensuring that the needle point does not spear the suture is to have the needle diameter be more than twice the suture diameter, so that the pointed face that interfaces with the suture puts the needle point above the profile of the suture diameter. This, however is a limitation, in that the hole left by the needle as it penetrates the soft tissues is considerably larger than the suture material left in its place.

Although an apparatus for the placement of mattress stitches has been disclosed here, instruments for other stitches, for example, a simple stitch, require only a single needle. Such instruments comprising only a single needle, or, in other instances, perhaps more than two needles, are within the scope of the present invention.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suturing device, comprising:
   a suture cartridge, the suture cartridge comprising a molded tip having a groove which is engageable with a length of suture;
   a needle which is axially movable distally and proximally substantially along a longitudinal axis;
   a soft tissue receiving recess disposed proximally of said suture cartridge, the soft tissue receiving recess defined by a soft tissue clamping mechanism, wherein the clamping mechanism comprises at least one movable jaw, and wherein the needle is axially movable around the at least one movable jaw; and
   the molded tip having a ramp portion disposed proximal to said groove and distal to said soft tissue receiving recess for re-directing said needle radially inwardly and outwardly with respect to said suture cartridge as the needle moves axially over said ramp portion wherein said needle comprises a distal point and said distal point is movable from a first retracted position, proximal to said soft tissue receiving recess, to a second extended position distal to said soft tissue receiving recess and said groove, wherein said needle engages the ramp portion and the distal point is deflected away from the length of suture in moving from the first retracted position to the second extended position.

2. The suturing device as recited in claim 1, wherein said clamping mechanism comprises a first jaw and a second jaw, wherein one of said jaws is movable relative to the other of said jaws to grasp soft tissue therein.

3. The suturing device as recited in claim 1, wherein said ramp portion comprises a radially outwardly sloping entrance ramp for moving said distal point radially outwardly as the needle moves axially in a distal direction.

4. The suturing device as recited in claim 1, wherein said needle comprises the distal point, a proximal shaft, and a hook defining a suture holding area.

5. The suturing device as recited in claim 4, and further comprising a terminus of said hook, said hook terminus being cantilevered proximally from a distal end of said needle.

6. The suturing device as recited in claim 5, and further. comprising a bump on said needle in a location opposed to said hook terminus.

7. The suturing device as recited in claim 6, wherein said hook terminus and said bump together provide a tactile sensation to a user when suture passes thereover into said suture holding area.

8. The suturing device as recited in claim 1, and further comprising a second needle.

9. The suturing device as recited in claim 1, further comprising a moveable sliding needle sheath for the needle to slide freely through, wherein the sheath selectively covers the needle so as to allow for smooth retraction of the needle.

10. A method of suturing soft tissue using a suturing device, said method comprising:
    retaining a portion of soft tissue to be sutured between a stationary jaw and a movable jaw;
    moving a slidable sheath and a needle such that the needle moves around the movable jaw , the needle having a suture holding tip substantially axially distally and substantially along a longitudinal axis through said portion of soft tissue, so that said needle and said sheath are deflected by a ramp portion of a suture cartridge radially outwardly away from a length of suture disposed on the suture cartridge of said suturing device, the suture cartridge comprising a molded tip having a groove, and so that said suture holding tip is disposed in a location along said longitudinal axis and distally past said portion of soft tissue and past the length of suture which is retained on the groove of said molded tip;
    moving said suture holding tip of said needle proximally and substantially along said longitudinal axis and capturing said suture so that it is retained in said suture holding area; and
    moving said needle a further distance proximally, so that said needle draws said suture through said portion of soft tissue, thereby suturing said soft tissue.

11. The method as recited in claim 10, wherein said suture holding tip is moved radially outwardly in order to avoid contacting said length of suture.

12. The method as recited in claim 10, wherein when said suture holding tip is moved proximally, it is also moved radially inwardly in order to ensure proper capture of said suture.

13. The method as recited in claim 10, and further comprising a step of covering said needle with the sheath prior to retracting the needle proximally through said soft tissue.

14. A suture cartridge detachably connectable to a distal portion of a suturing device for placing a suture in tissue, the suturing device has a tissue receiving recess proximal to said suture cartridge, said suture cartridge comprising a tip comprising a groove, and a suture threaded on said groove, and further comprising a needle-directing feature on said tip disposed proximal to said groove, said needle-directing feature comprising a surface disposed distal to said tissue receiving recess that deflects a distal end of a first needle of said suturing device radially outwardly away from a the suture as said first needle is extended distally along an substantially longitudinal axial pathway and wherein said suture cartridge further comprises a needle-retracting feature comprising a retraction surface that directs the needle distal end under the suture to capture the suture in the distal end of the first needle as the first needle is retracted proximally along the substantially longitudinal axial pathway.

15. The suture cartridge of claim 14 wherein said suture is threaded on said groove such that at least one suture end is presented for capture by the first needle.

16. The suture cartridge of claim 14 wherein said tip is configured to hold a first suture end and a second suture end such that said first and second suture ends may be captured by the first needle and a second needle respectively of said suturing device when said first and second needles are withdrawn through a tissue portion.

17. The suture cartridge of claim 14 wherein said needle-directing feature comprises a ramp.

18. The suture cartridge of claim 14 wherein said suture cartridge is adapted to be affixed to a first jaw of the distal portion of the suturing device.

19. The suture cartridge of claim 18 wherein said first jaw is fixed and lower than a second movable jaw of said suturing device.

* * * * *